US008559589B2

(12) United States Patent
Pinter et al.

(10) Patent No.: US 8,559,589 B2
(45) Date of Patent: Oct. 15, 2013

(54) WAVEGUIDE AND COMPUTED TOMOGRAPHY SYSTEM WITH A WAVEGUIDE

(75) Inventors: Robert Pinter, Aachen (DE); Jens Muehlsteff, Aachen (DE); Jeroen Adrianus Johannes Thijs, Waldfeucht (DE)

(73) Assignee: Koninklijke Philips N.V., Eindhoven (NL)

( * ) Notice: Subject to any disclaimer, the term of this patent is extended or adjusted under 35 U.S.C. 154(b) by 409 days.

(21) Appl. No.: 12/933,155

(22) PCT Filed: Mar. 12, 2009

(86) PCT No.: PCT/IB2009/051037
§ 371 (c)(1),
(2), (4) Date: Sep. 17, 2010

(87) PCT Pub. No.: WO2009/115958
PCT Pub. Date: Sep. 24, 2009

(65) Prior Publication Data
US 2011/0019792 A1    Jan. 27, 2011

(30) Foreign Application Priority Data

Mar. 19, 2008  (EP) .................................. 08152969

(51) Int. Cl.
*A61B 6/00* (2006.01)
(52) U.S. Cl.
USPC .......................................................... 378/8
(58) Field of Classification Search
USPC .......... 378/8; 333/239, 137; 600/425; 342/22
See application file for complete search history.

(56) References Cited

U.S. PATENT DOCUMENTS 4,463,329 A * 7/1984 Suzuki .......................... 333/239
4,800,350 A * 1/1989 Bridges et al. ................ 333/239
(Continued)

FOREIGN PATENT DOCUMENTS

| GB | 906206 A | 9/1962 |
| GB | 2399601 A | 9/2004 |
| JP | 2001053509 A | 2/2001 |
| WO | 0241776 A1 | 5/2002 |
| WO | 2006130798 A2 | 12/2006 |
| WO | 2007010422 A2 | 1/2007 |

OTHER PUBLICATIONS

Chen et al: "An X-Band Microwave Life-Detection System"; IEEE Transactions on Biomedical Engineering, vol. BME-33, No. 7, Jul. 1986, pp. 697-701.

(Continued)

*Primary Examiner* — Irakli Kiknadze

(57) ABSTRACT

The invention relates to a waveguide (24) for focusing electromagnetic energy on an area of interest, said waveguide (24) comprising outer walls forming a channel with a width (w) and a height (h) for the propagation of the electromagnetic waves. In order to be able to focus the EM waves on an area of interest, i.e. the chest of a patient (20), so that influences which other moving objects in the environment have on the waves, are shielded away, the channel is provided with a first opening and a second opening wherein said walls are non-metal hollow walls filled with an electrically conductive liquid. The waveguide (24) can be used for example with a computed tomography system (12) CT with a rotating gantry (16) and a patient table (18). The waveguide (24) will not produce artefacts in the CT image by scattering the X-ray, like a metal wall would do it. Nevertheless the conductive liquid makes the construction work as a waveguide for EM waves.

19 Claims, 2 Drawing Sheets

(56) References Cited

U.S. PATENT DOCUMENTS

| | | | |
|---|---|---|---|
| 5,227,797 | A | 7/1993 | Murphy |
| 7,755,055 | B2 * | 7/2010 | Schilling .................. 250/370.09 |
| 2003/0195413 | A1 | 10/2003 | Rubin et al. |
| 2003/0227360 | A1 * | 12/2003 | Kirihara et al. ............... 333/239 |
| 2004/0015087 | A1 | 1/2004 | Boric-Lubecke et al. |
| 2005/0007289 | A1 * | 1/2005 | Zarro et al. ................... 343/786 |
| 2005/0024167 | A1 | 2/2005 | Rawnick et al. |
| 2007/0109178 | A1 | 5/2007 | Schultheiss |

OTHER PUBLICATIONS

Zhou et al: "Detection of Multiple Heartbeats Using Doppler Radar"; IEEE, ICASSP, 2006, pp. 1160-1163.

Bruno et al: "Powder Core Dielectric Channel Waveguide"; IEEE Transactions on Microwave Theory and Techniques, vol. 42, No. 8, Aug. 1994, pp. 1524-1532.

* cited by examiner

WAVEGUIDE AND COMPUTED TOMOGRAPHY SYSTEM WITH A WAVEGUIDE

FIELD OF THE INVENTION

The invention relates to a waveguide, particularly a CT-compatible waveguide.

BACKGROUND OF THE INVENTION

Movement of an object during imaging modalities like CT has a negative influence on the quality of the obtainable images. Specifically while taking images of creatures, especially human beings, the quality of images suffers from motion artefacts induced by the beating heart. Therefore, one tries to determine those time periods when there is no such motion, and to do the imaging then. This technique is called gating. Today, the trigger signal for the image acquisition is usually derived from the ECG signal of the patient. Using the ECG signal for gating purposes means looking at the electrical excitation of the heart. Of course, the electrical excitation of the heart is correlated with its mechanical action. However, the reaction time of the heart muscle is unknown and varies. Because of that uncertainty and in order to be on the safe side, the period of time that is predicted to be the next resting phase of the heart has to be shortened by a certain amount of time. In other words, by looking at the ECG for gating purposes, one has to give away valuable data acquisition time simply because ECG is not a precise indicator of the true mechanical action of the heart. If the resting phases of the heart could be estimated better, and if they could thereby be fully exploited for the data acquisition, the total acquisition time could be shortened and the X-ray load imposed on the patient could be reduced. But in order to do that, one has to look directly at the mechanical action of the heart for which different methods are used. It is possible to measure the motion of a patient's heart and chest from a distance with the help of electromagnetic waves, in particular Doppler radar. However, Doppler radar responds to more than the heart motion alone. Because the Doppler radar sensor radiates electromagnetic waves in a broad radiation pattern, all moving parts around the sensor produce artefacts on the sensor signal. In current computer tomography (CT) systems, it is in particular the rotating gantry that produces low-frequency artefacts in the Doppler radar signal. The problem of artefacts due to the body's movement also occurs during MRI imaging. The document US 2003/0195413 A1 (Rubin, Jonathan M. et al.) unveils an MRI system with a detector system used for producing a gating signal for the MRI system. The detector system comprises an ultrasonic transducer for detecting movement of the object while the images are being acquired by the means of the MRI system. In one embodiment an acoustic waveguide is used that extends into the bore of magnet in order to place the transducer outside the field of the MRI system. In WO 02/41776 A1 (Feinberg, David) it is further proposed to use ultrasound to determine the position of the moving organ and to translate the new parameters into an angulation and displacement of the subsequently acquired MRI image volume. But it has shown that with the means of ultrasonic sound the resolution being obtainable for deeper tissue structure is less compared with CT- or MRI-systems. Also, the coupling of the acoustic waves into the body requires an acoustic coupling medium which may result in false signals and which is undesired in respect of user-comfort. Especially for investigating the human heart with the means of ultrasonic sound, only specific so-called ultrasonic windows can be used through which a direct acoustic path to the heart is possible due to the human anatomy. Outside these windows reflections can be caused by the lung or by bone-structures. This means that for ultrasonic investigations of the heart, experience is required to be able to place the transducer properly. Hence there still is a need for a more precise indicator of the actual mechanical action of the heart.

SUMMARY OF THE INVENTION

It is an object of the invention to provide an improved gating signal.

The object is reached with a waveguide comprising outer walls forming a channel for the propagation of the electromagnetic waves, said channel having a first opening and a second opening wherein said walls are non-metal hollow walls filled with an electrically conductive liquid or gel.

The use of electromagnetic waves like radar has the advantage that these are reflected on barrier layers between areas of different electric conductivity. Within the thorax this is most significant the case at the cardiac wall (myocard). It is an advantage of the invention that the EM waves can be focused on an area of interest, such as the chest of a patient, so that influences which other moving objects in the environment have on the waves are shielded away. By providing a non-metal (e.g. plastic) waveguide with hollow walls that are filled with an electrically conductive liquid such as salt water, the conductive liquid will not produce artefacts in the CT image by scattering the X-ray, like a metal wall would do it. Nevertheless the conductive liquid makes the construction work as a waveguide for EM waves.

In one embodiment of the invention, the width and the height of the channel and the channel openings are tailored to the frequency of the electromagnetic waves that are to be transported through the channel. In a further embodiment of the invention the width is basically equal to two times the height to allow an optimal propagation of the EM.

The object is further reached with an apparatus comprising a radar sensor emitting electromagnetic waves said radar sensor including an antenna, a control unit and at least one waveguide according to one of the aforementioned embodiments for the focusing of said electromagnetic waves on an area of interest of a subject to be examined, said at least one waveguide having its first opening oriented towards the radar sensor.

In one embodiment of the invention the radar sensor is a Doppler radar sensor which allows a reliable and precise detecting of movements.

In one further embodiment of the invention a distance piece is located between the radar antenna and the subject to be examined, wherein said distance piece is formed by said at least one waveguide. The distance piece keeps the distance between Doppler radar antenna and chest wall constant. This way, there is no motion of the chest wall relative to the sensor, so that only the moving heart wall contributes to the Doppler shift and not the chest wall. Thus the Doppler shifts that would normally occur due to motion of the chest wall relative to the radar antenna are effectively eliminated. This results in the information about the heart wall motion being immediately available in the signal.

Preferably a support device is provided upon which the subject to be examined can be placed temporarily to allow an easy investigation without the necessity of holding the subject.

Further preferred is an embodiment where the subject to be examined is a patient and the support device is a patient table to receive the patient. Although Doppler radar can be used for the detecting of different moving objects, one of the major areas of measurements with Doppler radar is within healthcare.

Still further preferred is an embodiment wherein the at least one waveguide is located within the patient table in order to obstruct the patient as little as possible. Moreover also the radar sensor and/or the control unit can be installed in the patient table, which allows a compact design and an easy installation.

In a further preferable embodiment multiple waveguides form an array of waveguides to achieve more tolerance with respect to the patient position, for example on the patient table. After the patient is positioned on the table, a control unit tests the signals from all sensors in the array and selects the best one for the subsequent measurement. By using multiple radar sensors to feed the waveguide array the control unit is able to test the signals from all sensors in the array and to select the best one for the subsequent measurement.

The problems discussed above can preferably be improved by a computed tomography system with a rotating gantry, said computed tomography system comprising a system control, an apparatus according to one of the preceding embodiments and a waveguide according to one of the aforementioned embodiments wherein the apparatus detects motion in the patient motion due to respiration or due to the blood pumping of the heart and provides a gating signal to the system control, said gating signal triggering the acquisition of CT data.

These and other aspects of the invention will be apparent from and elucidated with reference to the embodiment(s) described hereinafter.

DETAILED DESCRIPTION OF EMBODIMENTS

Figure 1:
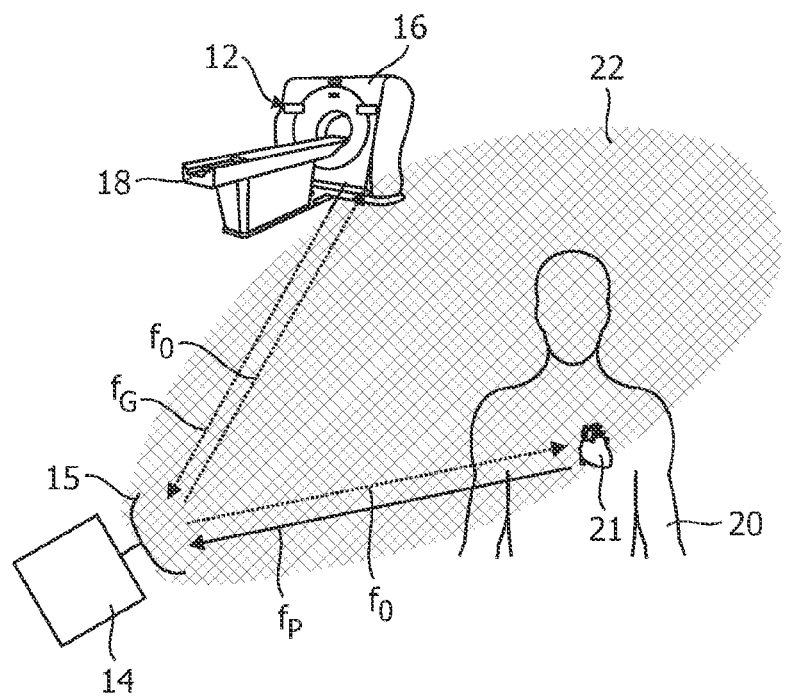
FIG. 1 is a schematic diagram of a Doppler radar sensor in a CT environment, picking up heart wall motion, chest wall motion and gantry motion.

FIG. 1 schematically shows the background of the invention. To provide a gating signal a CT system 12 is provided with a Doppler radar sensor 14 with an antenna 15. The CT system 12 comprises a rotating gantry 16 and a support device 18, i.e. a patient table, to receive a patient 20 whose heart 21 is to be examined for generating a gating signal for the CT system 12. As can be seen the Doppler radar sensor 14 is used in order to pick up information on the heart wall motion of the patient 20. But the Doppler radar sensor 12 also "sees" the rotating gantry 16 of the CT 12, because the sensor's area of sensitivity 22 is rather broad. The Doppler radar sensor 14 cannot differentiate between the reflections from the heart wall of the patient 20 and the reflections from the gantry 16, since both Doppler frequency shifts are almost the same. So the signals are superimposed and would be interpreted as resulting from a single target, which leads to wrong conclusions. In addition, there is a reflection from the chest wall of the patient 20, said reflection being strongly correlated with the heart wall motion, but not identical. Compared to the reflection from the heart wall, the reflection from the chest wall is much stronger.

In FIG. 1 the signal sent by the Doppler radar sensor 14 is indicated by the arrows $f_0$.

The reflections from the gantry 16 are indicated by the arrow $f_G$:

$$f_G = f_0 + f_{Doppler\ gantry}$$

The reflections from the patient 20 are indicated by the arrow $f_P$ which comprises the reflections from the beating heart 21 and the moving chest:

$$f_{P\_heart} = f_0 + f_{Doppler\ heart}$$

$$f_{P\_chest} = f_0 + f_{Doppler\ chest}$$

Figure 2:
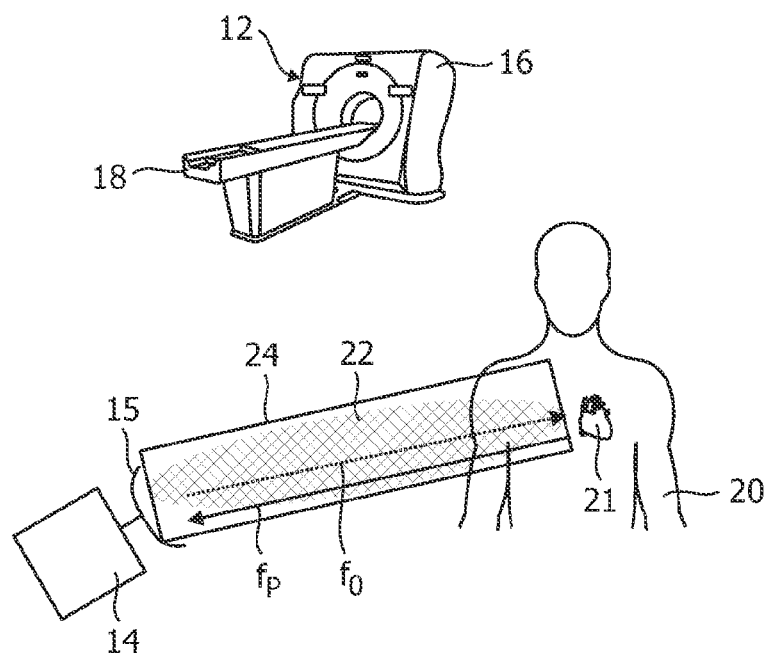
FIG. 2 is a schematic diagram of a setup of a Doppler radar sensor picking up heart wall motion in a CT environment, with a waveguide used as a distance piece according to the invention.

In FIG. 2 a waveguide 24 according to the invention focuses all of the available radiated electromagnetic power from the Doppler radar sensor 14 on the area of interest, in this case the patient's chest. Focusing the electromagnetic waves also means focusing or narrowing the resulting sensor's area of sensitivity 22. The waveguide 24 also shields away external influences from the electromagnetic waves propagating inside of it.

The Doppler shift generated by the chest wall motion occurs due to relative motion between the chest wall and the antenna 15 of the Doppler radar sensor 14. So if the waveguide 24 is used as a distance piece between the antenna 15 and the patient's chest wall, the relative motion between the two is eliminated and the Doppler radar sensor 14 directly delivers information on the mechanical action of the heart wall alone.

In FIG. 2 the signal sent by the Doppler radar sensor 14 is indicated by the arrows $f_0$ as is the case in FIG. 1. Due to the waveguide 24 there are no reflections from the gantry 16. The reflections from the patient 20 are reduced to the reflections by the beating heart 21 since the waveguide 24 acts as a distance piece so that the moving chest of the patient 20 does not result in Doppler shifts, since the distance between the Doppler radar sensor 14 and the patient 20 is being kept constant, i.e. there is no relative motion between the two. The reflections from the beating heart 21 are indicated by the arrow $f_P$, according to FIG. 1:

$$f_P = f_0 + f_{Doppler\ heart}$$

FIG. 2 also illustrates the principle how the waveguide 24 is installed, namely between the antenna 15 of the radar sensor 14 and the thorax of the patient 20. Of course it is possible to do that in the way suggested by FIG. 2, by resting one end of the waveguide 24 on the chest of the patient 14. However, a setup is also provided in which the waveguide 24 is installed in a more unobtrusive way. Therefore a setup (not shown) is provided where the radar sensor 14 with the antenna 15 and the waveguide 24 are installed directly in the patient table 18.

Figure 3:
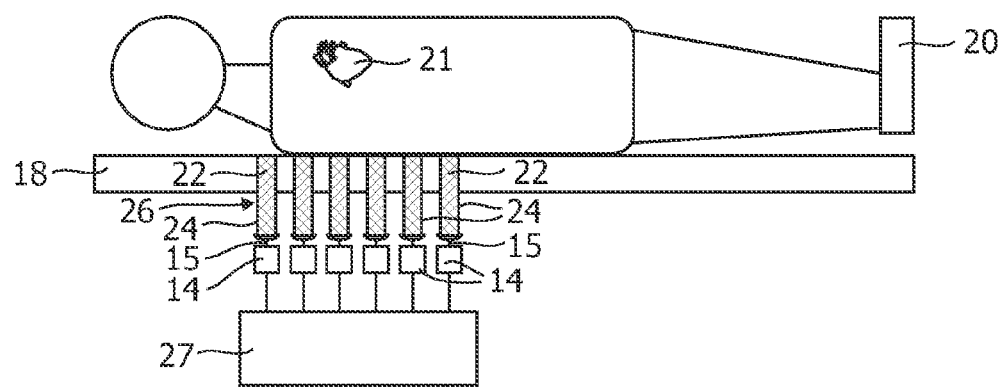
FIG. 3 is a schematic longitudinal section of a setup with an array of waveguides and radar sensors integrated in a patient table.

It is furthermore proposed to install not just a single waveguide 24 and radar sensor 14 in the patient table 18, but an array 26, of which the setup is shown in FIG. 3 where the radar sensors 14 and the waveguides 24 are installed directly in the patient table 18.

By using the array 26 of waveguides 24 and radar sensors 14, more tolerance with respect to the position of the patient 20 is achieved. After the patient 20 is positioned on the table 18, a control unit 27 tests the signals from all sensors 14 in the array 26 and selects the best one for the subsequent measurement of the beating heart 21.

No matter which of the setups described above is chosen, there is one common issue, namely the fact that the waveguide 24 is always positioned in the sensitive area of the CT scanner 12. There are special requirements in CT imaging environments regarding metal, because larger pieces of metal materials have a negative effect on the CT imaging quality. The scattering effect of metals on the X-ray radiation produces streak artefacts in the image. The present invention solves that problem by providing the non-metal waveguide 24, suitable for the particular operating frequency of the Doppler radar 14.

The best-known non-metal waveguide for EM waves is a glass fibre. This type of waveguide is called a dielectric waveguide, and because it doesn't contain metal, dielectric waveguides are in principle suited for the usage in a CT environment. However, waveguides for EM waves have to be tailored to the frequency of the EM waves. The abovementioned glass fibres, for example, function as waveguides only for a certain range of optical wavelengths. For frequencies higher than several 10 GHz, designing a dielectric waveguide is well feasible. However, the investigations conducted at the Philips research laboratory in Aachen revealed that in particular a frequency as low as 2.45 GHz is a very favourable one for looking at the heart wall motion. It is practically impossible to realize a dielectric waveguide that operates at this frequency, because materials with extremely high dielectric constants would have to be used. In William M. Bruno, William B. Bridges: "Powder Core Dielectric Channel Waveguide"; IEEE Transactions on microwave theory and techniques, Vol. 42, no. 8, August 1994, experiments are described with AlNi titanate powders being used as such material, but again only for very high frequencies.

Figure 4:
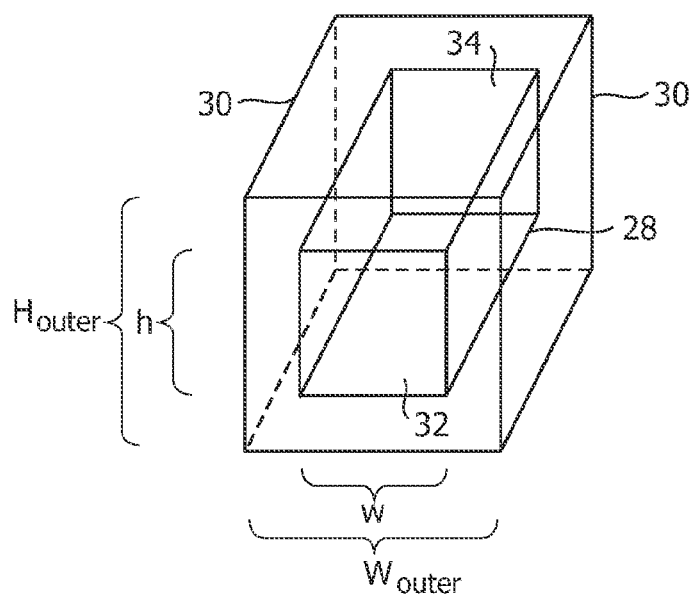
FIG. 4 is showing the construction of the non-metal waveguide according to the invention and FIG. 5 is showing a common waveguide made of metal.
Figure 5:
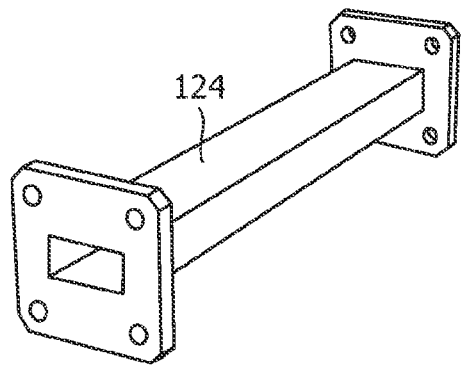

The type of waveguide 24 according to the present invention is shown in FIG. 4 and a commonly used waveguide 124 according to the state of the art is shown in FIG. 5. Just like in an ordinary metal waveguide 124 (FIG. 5), the waveguide 24 according to the present invention shows a channel 28 with surrounding walls 30 and two openings 32, 34. The electromagnetic waves propagate through said channel 28 whose width w and height h have to be tailored to the frequency of the electromagnetic waves that are to be transported through the channel 28. Typically, the width w is equal to two times the height h, or very close to that value.

The walls 30 are made of plastic, but are hollow and contain a highly conductive non-metal fluid (e.g. salt water, not shown). The conductive liquid will not produce artefacts in the CT image by scattering the X-ray, like a metal wall would do it. Nevertheless the conductive liquid will make the construction work as a waveguide for electromagnetic waves.

Besides the theory behind the construction of waveguides which is commonly known, in the following some equations will be given for completeness.

$$f_{lower\_cutoff} = \frac{c}{\lambda_{lower\_cutoff}} = \frac{c}{2 \cdot w}$$

$$w = 2 \cdot h$$

Rectangular waveguides exhibit a lower cut-off frequency, $f_{lower\_cutoff}$ in the formula above, below which they don't act as a waveguide. This lower cut-off frequency determines the width w of the channel 28 guiding the waves. In rectangular waveguides 24, the height h can be easily determined, once the width w is calculated.

If the channel width w and the channel height h are determined according to the EM wave frequency, the outer dimensions of the waveguide 24, i.e. the outer width $W_{outer}$ and the outer height $H_{outer}$, can be defined. Together with the channel width and height parameters w and h, the outer dimensions $W_{outer}$ and $H_{outer}$ determine the wall thickness. The thickness of the walls 30 determines the quality of shielding that the waveguide 24 provides against influences of movements in the environment of the waveguide 24 that would disturb the EM waves propagating inside the channel 28.

The common example of the waveguide 124 known in the state of the art shown in FIG. 5 is typically made of metal. In principle, it is a metal pipe through which the electromagnetic waves propagate. The dimensions of the waveguide 124 determine the propagation properties of the electromagnetic waves inside the waveguide 124.

This invention can be applied in any application where a radar sensor or other sensor that depends on electromagnetic waves is used to capture body signals in an environment with other moving objects. A special case is using the radar sensor for gating of cardiac CT or other imaging modalities where this problem occurs.

While the invention has been illustrated and described in details in the drawings and forgoing description, such illustration and description are to be considered illustrative or exemplary and not restrictive; the invention is not limited to the disclosed embodiments.

The invention claimed is:

1. An apparatus comprising a radar sensor emitting electromagnetic waves said radar sensor including an antenna, a control unit and at least one waveguide for the focusing of the electromagnetic waves on an area of interest of a subject to be examined, wherein the waveguide includes outer walls forming a channel with a width and a height for propagation of the electromagnetic waves, the channel having a first opening and a second opening, wherein the walls are non-metal hollow walls filled with an electrically conductive liquid or gel, and the at least one waveguide having the first opening oriented towards the radar sensor.

2. The waveguide according to claim 1, wherein the width- and the height of the channel and the channel openings are tailored to the frequency of the electromagnetic waves that are to be transported through the channel.

3. The waveguide according to claim 2, wherein the width is basically equal to two times the height.

4. The apparatus according to claim 1, wherein the radar sensor is a Doppler radar sensor.

5. The apparatus according to claim 1, wherein a distance piece is located between the radar antenna and the subject to be examined, whereby said distance piece is formed by said at least one waveguide.

6. The apparatus according to claim 1, wherein a support device is provided upon which the subject to be examined is placed temporarily.

7. The apparatus according to claim 6, wherein the subject to be examined is a patient and the support device is a patient table to receive the patient.

8. The apparatus according to claim 7, wherein the at least one waveguide is located within the patient table.

9. The apparatus according to claim 8, wherein the radar sensor is installed in the patient table.

10. The apparatus according to claim 7, wherein the control unit is installed in the patient table.

11. The apparatus according to claim 1, wherein multiple waveguides form an array of waveguides.

12. The apparatus according to claim 11, wherein multiple radar sensors are used feeding the waveguide array.

13. A computed tomography system with a rotating gantry, said computed tomography system comprising: a system control, and an apparatus, comprising: a radar sensor emitting electromagnetic waves, the radar sensor including an antenna, a control unit and at least one waveguide for focusing electromagnetic energy on an area of interest, the waveguide comprising outer walls forming a channel with a width and a height for propagation of the electromagnetic waves, the channel having a first opening and a second opening, and the at least one waveguide having the first opening oriented towards the radar sensor, wherein the walls are non-metal hollow walls filled with an electrically conductive liquid or gel, wherein the apparatus detects motion in a patient due to respiration or due to blood pumping of the heart and provides a gating signal to a system controlling the gating signal triggering an acquisition of CT data.

14. A method, comprising:
focusing, via a waveguide of a radar sensor of an apparatus, electromagnetic energy on an area of interest, said waveguide comprising outer walls forming a channel with a width and a height for the propagation of the electromagnetic waves, said channel having a first opening and a second opening, wherein said walls are non-metal hollow walls filled with an electrically conductive liquid or gel and the first opening oriented towards the radar sensor, and the radar sensor emitting the electromagnetic energy and further including an antenna and a control unit.

15. The method according to claim 14, wherein the width and the height of the channel and the channel openings are tailored to the frequency of the electromagnetic waves that are to be transported through the channel.

16. The method according to claim 15, wherein the width is basically equal to two times the height.

17. The method according to claim 15, wherein the waveguide is located within a patient table.

18. The method according to claim 15, wherein a support device is provided upon which a subject to be examined is placed temporarily.

19. The method according to claim 18, wherein the subject to be examined is a patient and the support device is a patient table to receive the patient.

* * * * *